United States Patent
Leahy et al.

(10) Patent No.: US 9,718,845 B2
(45) Date of Patent: Aug. 1, 2017

(54) PROCESS FOR THE PREPARATION OF CYCLOHEPTAPYRIDINE CGRP RECEPTOR ANTAGONISTS

(71) Applicant: BRISTOL-MYERS SQUIBB COMPANY, Princeton, NJ (US)

(72) Inventors: David K. Leahy, Hightstown, NJ (US); Yu Fan, Highland Park, NJ (US); Collin Chan, New York, NY (US); Lopa V. Desai, Chesterfield, NJ (US); Sunil S. Patel, Edison, NJ (US); Masano Sugiyama, Cranbury, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/225,261

(22) Filed: Aug. 1, 2016

(65) Prior Publication Data

US 2016/0340373 A1  Nov. 24, 2016

Related U.S. Application Data

(60) Continuation of application No. 14/833,891, filed on Aug. 24, 2015, now abandoned, which is a continuation of application No. 14/568,370, filed on Dec. 12, 2014, now abandoned, which is a continuation of application No. 14/156,626, filed on Jan. 16, 2014, now abandoned, which is a division of application No. 13/236,072, filed on Sep. 19, 2011, now Pat. No. 8,669,368.

(60) Provisional application No. 61/392,183, filed on Oct. 12, 2010.

(51) Int. Cl.
| | |
|---|---|
| C07D 221/06 | (2006.01) |
| C07D 221/16 | (2006.01) |
| C07F 7/18 | (2006.01) |
| C07D 221/04 | (2006.01) |
| C07D 471/04 | (2006.01) |

(52) U.S. Cl.
CPC .......... C07F 7/1856 (2013.01); C07D 221/04 (2013.01); C07D 471/04 (2013.01); C07F 7/1844 (2013.01); C07F 7/1868 (2013.01)

(58) Field of Classification Search
CPC .............................. C07D 221/06; C07D 221/16
USPC ......................................................... 546/112
See application file for complete search history.

(56) References Cited

U.S. PATENT DOCUMENTS

| | | | |
|---|---|---|---|
| 8,314,117 B2 * | 11/2012 | Luo | C07D 401/12 514/278 |
| 8,669,368 B2 | 3/2014 | Leahy et al. | |
| 2013/0053570 A1 * | 2/2013 | Luo | C07D 401/12 546/118 |
| 2014/0135500 A1 | 5/2014 | Leahy et al. | |
| 2015/0099887 A1 | 4/2015 | Leahy et al. | |

FOREIGN PATENT DOCUMENTS

| | | |
|---|---|---|
| WO | WO2007016087 A2 | 2/2007 |
| WO | WO2007120590 A2 | 10/2007 |
| WO | WO2009126530 A2 | 10/2009 |
| WO | WO2011046997 A1 | 4/2011 |
| WO | WO2012050764 A1 | 4/2012 |

OTHER PUBLICATIONS

U.S. Appl. No. 13/236,072, Information Disclosure Statement, Oct. 15, 2013.
U.S. Appl. No. 14/156,626, Information Disclosure Statement, Jun. 16, 2014.
U.S. Appl. No. 14/568,370, Information Disclosure Statement, May 22, 2015.
U.S. Appl. No. 14/833,891, Information Disclosure Statement, May 2, 2016.
WO2012050764, PCT Preliminary Report on Patentability, Apr. 16, 2013.
WO2012050764, PCT Written Opinion of ISA, Apr. 12, 2013.

* cited by examiner

*Primary Examiner* — Niloofar Rahmani
(74) *Attorney, Agent, or Firm* — James Epperson

(57) ABSTRACT

The disclosure generally relates to a process for the preparation of compounds of formula I, including synthetic intermediates which are useful in the process.

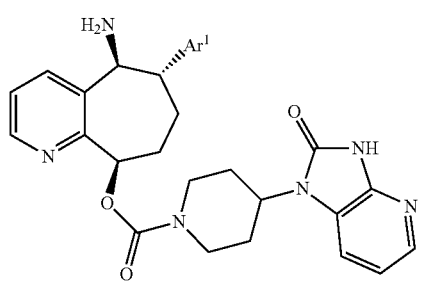

9 Claims, No Drawings

PROCESS FOR THE PREPARATION OF CYCLOHEPTAPYRIDINE CGRP RECEPTOR ANTAGONISTS

CROSS REFERENCE TO RELATED APPLICATIONS

This Continuation application claims the benefit of U.S. Ser. No. 14/833,891 filed Aug. 24, 2015, which is a Continuation application which claims the benefit of U.S. Ser. No. 14/568,370 filed Dec. 12, 2014, now abandoned, which is a Continuation application which claims the benefit of U.S. Ser. No. 14/156,626 filed Jan. 16, 2014, now abandoned, which is a Divisional application which claims the benefit of U.S. Ser. No. 13/236,072 filed Sep. 19, 2011, now U.S. Pat. No. 8,669,368, which is a Non-Provisional application which claims the benefit of Provisional application U.S. Ser. No. 61/392,183 filed Oct. 12, 2010, hereby incorporated by reference in their entireties.

BACKGROUND OF THE INVENTION

The disclosure generally relates to a synthetic process for preparing compounds of formula I including the preparation of chemical intermediates useful in this process.

CGRP inhibitors are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP antagonists have shown efficacy in human clinical trials. See Davis C D, Xu C. *Curr Top Med Chem.* 2008 8(16):1468-79; Benemei S, Nicoletti P, Capone J G, Geppetti P. *Curr Opin Pharmacol.* 2009 9(1):9-14. Epub 2009 Jan. 20; Ho T W, Ferrari M D, Dodick D W, Galet V, Kost J, Fan X, Leibensperger H, Froman S, Assaid C, Lines C, Koppen H, Winner P K. *Lancet.* 2008 372:2115. Epub 2008 Nov. 25; Ho T W, Mannix L K, Fan X, Assaid C, Furtek C, Jones C J, Lines C R, Rapoport A M; *Neurology* 2008 70:1304. Epub 2007 Oct. 3.

CGRP receptor antagonists have been disclosed in PCT publications WO 2004/092166, WO 2004/092168, and WO 2007/120590. The compound (5S,6S,9R)-5-amino-6-(2,3-difluorophenyl)-6,7,8,9-tetrahydro-5H-cyclohepta[b]pyridin-9-yl 4-(2-oxo-2,3-dihydro-1H-imidazo[4,5-b]pyridin-1-yl)piperidine-1-carboxylate is an inhibitor of the calcitonin gene-related peptide (CGRP) receptor.

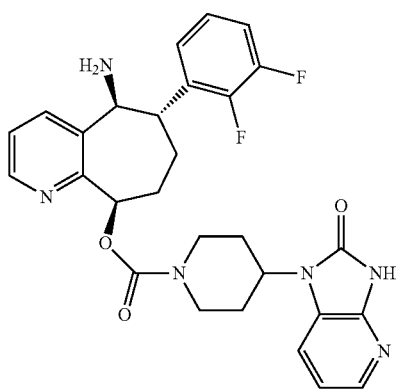 [SMILES: N[C@@H]1c2cccnc2[C@H](OC(=O)N2CCC(n3c(=O)[nH]c4ncccc43)CC2)CC[C@H]1c1cccc(F)c1F]

For purposes of large-scale production there is a need for a high-yielding synthesis of compound of formula I and related analogs that is both efficient and cost-effective.

DESCRIPTION OF THE INVENTION

One aspect of the invention is a process for the preparation of a compound of formula I, or a salt thereof, where $Ar^1$ is phenyl substituted with 0-3 substituents selected from the group consisting of cyano, halo, alkyl, haloalkyl, alkoxy, haloalkoxy, and $alkylSO_2$

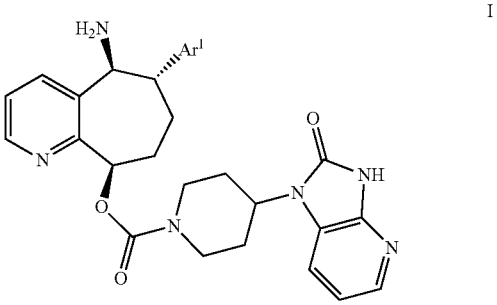

I comprising the reductive amination and alcohol deprotection of a compound of formula IV where $R^1$ is selected from the group consisting of trialkylsilyl, alkoxy, alkylcarbonyl, benzyl, substituted benzyl, benzoyl, and pivaloyl to a compound of formula II where $R^1$ is hydrogen, and coupling the compound of formula II, or a salt thereof, with a compound of formula III where $R^2$ is selected from the group consisting of imidazolyl, pyrrolyl, N-hydroxysuccinimidyl, chloro, phenoxy, substituted phenoxy, phenylthio, and substituted phenylthio.

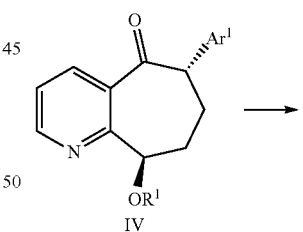

IV

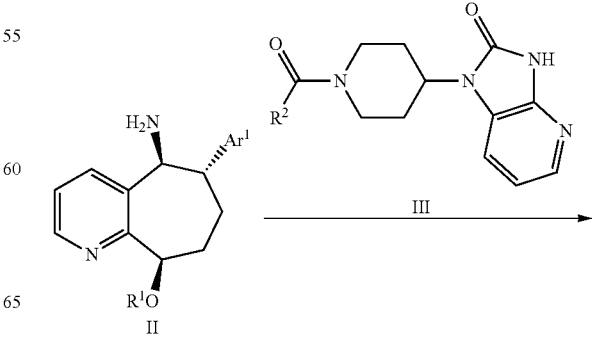

II

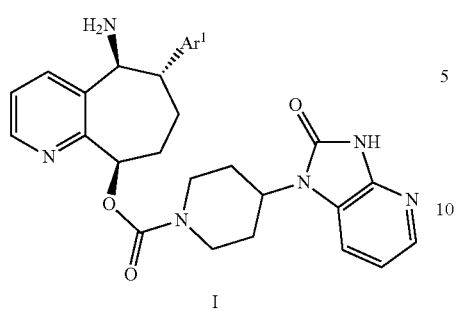

I

Another aspect of the invention is a process for the preparation of a compound of formula I, or a salt thereof, where $Ar^1$ is phenyl substituted with 0-3 substituents selected from the group consisting of cyano, halo, alkyl, haloalkyl, alkoxy, haloalkoxy, and alkylSO$_2$

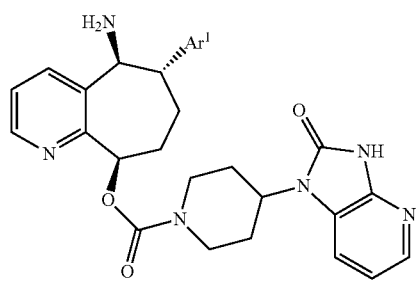

I comprising coupling a compound of formula II, or a salt thereof, where $R^1$ is hydrogen, or a salt thereof, with a compound of formula III, or a salt thereof, where $R^2$ selected from the group consisting of imidazolyl, pyrrolyl, N-hydroxysuccinimidyl, chloro, phenoxy, substituted phenoxy, phenylthio, and substituted phenylthio.

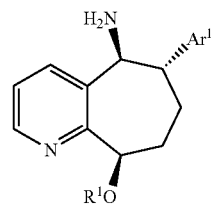

II

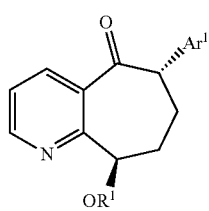

III

Another aspect of the invention is where the compound of formula II is

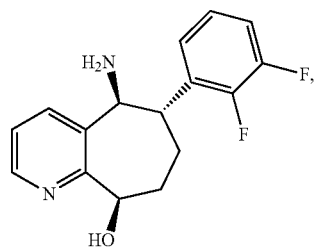 [SMILES: N[C@@H]1c2cccnc2[C@H](O)CC[C@H]1c1cccc(F)c1F]

or a salt thereof, and the compound of formula III is or a salt thereof.

Another aspect of the invention is a process for the preparation of a compound of formula II, or a salt thereof, where $Ar^1$ is phenyl substituted with 0-3 substituents selected from the group consisting of cyano, halo, alkyl, haloalkyl, alkoxy, haloalkoxy, and alkylSO$_2$ and $R^1$ is hydrogen,

II

IV comprising the reductive amination and deprotection of a compound of formula IV, or a salt thereof, where $Ar^1$ is phenyl substituted with 0-3 substituents selected from the group consisting of cyano, halo, alkyl, haloalkyl, alkoxy, haloalkoxy, and alkylSO$_2$ and $R^1$ is trialkylsilyl, alkoxy, alkylcarbonyl, benzyl, substituted benzyl, benzoyl, and pivaloyl.

Another aspect of the invention is a process where $Ar^1$ is 2,3-difluorophenyl and where $R^1$ is triisopropylsilyl for the compound of formula IV.

Another aspect of the invention is a process for the preparation of a compound of formula III, or a salt thereof, where $R^2$ is imidazolyl

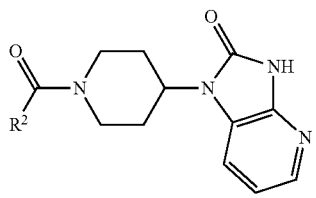

comprising coupling 3-N-piperidin-4-ylpyridine-2,3-diamine, or a salt thereof, or 1-(piperidin-4-yl)-1H-imidazo[4,5-b]pyridin-2(3H)-one, or a salt thereof, with carbonyl diimidazole or triphosgene and imidazole.

Another aspect of the invention is a compound of formula II, or a salt thereof, where $Ar^1$ is phenyl substituted with 0-3 substituents selected from the group consisting of cyano, halo, alkyl, haloalkyl, alkoxy, haloalkoxy, and $alkylSO_2$ and $R^1$ is hydrogen or trialkylsilyl, alkoxy, alkylcarbonyl, benzyl, substituted benzyl, benzoyl, and pivaloyl. Another aspect of the invention is a compound of formula II where $Ar^1$ is 2,3-difluorophenyl and $R^1$ is hydrogen or a salt thereof. Another aspect of the invention is a compound of formula II which is the dihydrochloride salt. Another aspect of the invention is a compound of or formula II where $Ar^1$ is 2,3-difluorophenyl and $R^1$ is triisopropylsilyl or a salt thereof. Another aspect of the invention is a compound of formula II which is the dihydrochloride salt.

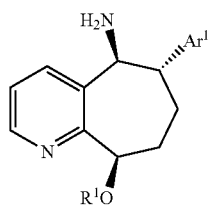

Another aspect of the invention is a compound of formula III, or a salt thereof, where $R^2$ is selected from the group consisting of imidazolyl, pyrrolyl, N-hydroxysuccinimidyl, chloro, phenoxy, substituted phenoxy, phenylthio, and substituted phenylthio. Another aspect of the invention is a compound of claim 12 where $R^2$ is imidazolyl.

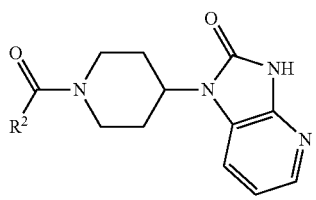

Unless specified otherwise, these terms have the following meanings. "Alkyl" means a straight or branched alkyl group composed of 1 to 6 carbons, preferably 1 to 3 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic ring systems.

Those skilled in the art understand that there are a variety of alternative reagents and solvents that can be interchanged. The following definitions are meant to serve as non-limiting examples to illustrate a term and are not meant to limit the definition to the examples listed.

Some suitable protecting groups at $R^1$ include trialkylsilyl, alkyl ether, benzyl ether, alkyl carbonate, benzyl carbonate, and ester. Trialkylsilyl includes TMS, TES, TIPS, TPS, TBDMS, and TBDPS. Alkyl ethers include methyl, MOM, BOM, PMBM, t-Butoxymethyl, SEM, THP, t-Bu, and allyl. Benzyl ether includes methoxybenzyl, dimethoxybenzyl, trifluoromethylbenzyl, nitrobenzyl, dinitrobenzyl, cyanobenzyl, and halobenzyl, diphenylmethyl and triphenylmethyl. Alkyl carbonate includes methyl, ethyl, isobutyl, vinyl, allyl and nitrophenyl. Substituted benzyl carbonate includes methoxybenzyl, dimethoxybenzyl and nitrobenzyl. Ester includes pivolate, adamantoate, benzoate, phenylbenzoate, and mesitoate.

Some suitable leaving groups at $R^2$ include imidazolyl, pyrrolyl, N-hydroxysuccinimidyl, chloro, substituted phenoxy, and substituted phenylthio. Substituted phenoxy includes nitrophenoxy, cyanophenoxy, and trifluoromethylphenoxy. Substituted phenylthio includes nitrophenylthio, cyanophenylthio, and trifluoromethylphenylthio.

Some suitable reductive amination conditions include using ammonia, hydroxyamine, protected hydroxyamine (for example, methoxyamine, benzyloxyamine, acetoxyamine), benzylamine, and the salts of these aminating reagents (for example, ammonium acetate, ammonium chloride). Benzyl includes methoxybenzyl, dimethoxybenzyl, trifluoromethylbenzyl, nitrobenzyl, dinitrobenzyl, cyanobenzyl, and halobenzyl, diphenylmethyl and triphenylmethyl.

Some suitable reagents for dehydrating agents in the reductive amination include titanium alkoxides, titanium chloride, mixed titanium alkoxides/chlorides, aluminum chloride, zirconium chloride, tin chloride, boron trifluoride, copper sulfate, magnesium sulfate, and molecular sieves. Titanium alkoxides include isopropoxide, propoxide, ethoxide, methoxide, butoxide, and t-butoxide.

Some suitable reduction conditions include transition metal catalyzed hydrogenations with for example, palladium, platinum, or iridium catalysts, metal hydrides of aluminum and boron, and zinc with acetic acid. Some catalysts include palladium on alumina, palladium on calcium carbonate, palladium-lead on calcium carbonate, palladium on carbon and Perlman's catalyst.

Some suitable acids for deprotecting the alcohol include any acid or fluoride containing reagent. For example, hydrogen chloride, hydrogen bromide, sulfuric acid, methanesulfonic acid, p-toluenesulfonic acid, trifluoroacetic acid, hydrogen fluoride, hydrogen fluoride-pyridine, and tetrabutylammonium fluoride.

Some suitable bases for the coupling include group I and II metal alkoxides (for example, sodium methoxide, potassium t-butoxide and sodium t-butoxide), group I metal disilazides (for example potassium disilazide), group I and II hydrides (for example, sodium hydride), group I amides (for example, lithium diisopropylamide), and group I metal alkydes (for example, butyl lithium).

Synthetic Methods

The following methods are for illustrative purposes and are not intended to limit the scope of the invention. Those skilled in the art understand that there will be a number of equivalent methods for the preparation of these compounds and that the synthesis is not limited to the methods provided in the following examples. For example, some reagents and solvents may have equivalent alternatives known to those in the art. The variables describing general structural formulas and features in the synthetic schemes are distinct from and should not be confused with the variables in the claims or the rest of the specification. These variables are meant only to illustrate how to make some of the compounds of the invention.

Abbreviations used in the description generally follow conventions used in the art. Some abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Scheme 1 illustrates a synthesis of formula I compounds.

Scheme 1.

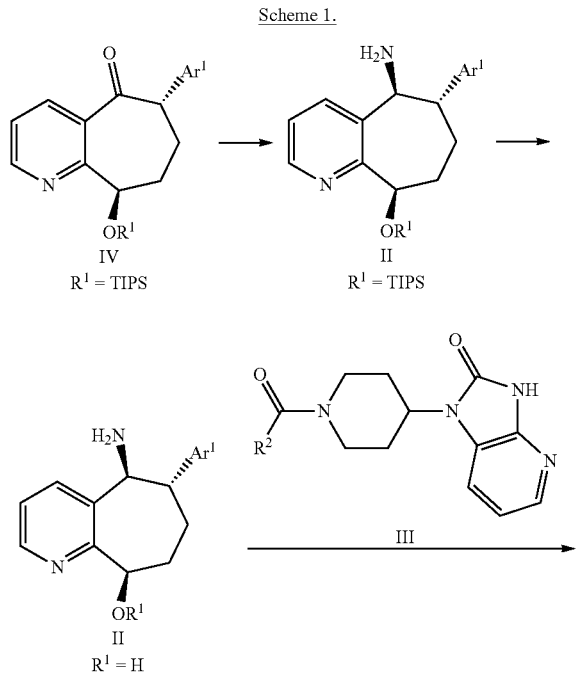

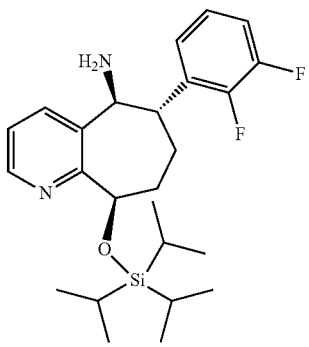 [SMILES: CC(C)[Si](O[C@@H]1CC[C@@H](c2cccc(F)c2F)[C@H](N)c2cccnc21)(C(C)C)C(C)C]

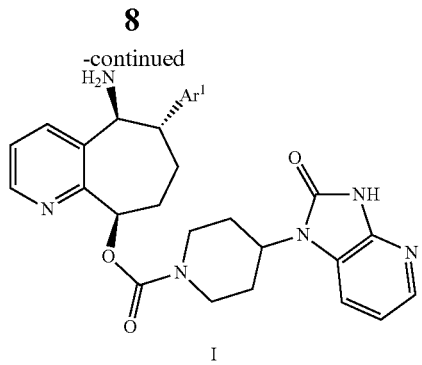

I

DESCRIPTION OF SPECIFIC EMBODIMENTS

Example 1

(6S,9R)-6-(2,3-difluorophenyl)-9-(triisopropylsilyloxy)-6,7,8,9-tetrahydro-5H-cyclohepta[b]pyridin-5-amine To a 100 mL hastelloy autoclave reactor was charged (6S,9R)-6-(2,3-difluorophenyl)-9-(triisopropylsilyloxy)-6,7,8,9-tetrahydro-5H-cyclohepta[b]pyridin-5-one (5.00 g, 11.22 mmol), 1,4-dioxane (50 mL) and titanium tetra(isopropoxide) (8.33 mL, 28.11 mmol). The reactor was purged three times with nitrogen and three times with ammonia. After the purge cycle was completed, the reactor was pressurized with ammonia to 100 psig. The reaction mixture was heated to 50° C. (jacket temperature) and stirred at a speed to ensure good mixing. The reaction mixture was aged at 100 psig ammonia and 50° C. for 20 h. The mixture was then cooled to 20° C. then 5% Pd/Alumina (1.0 g, 20 wt %) was charged to the autoclave reactor. The reactor was purged three times with nitrogen and three times with hydrogen. After the purged cycle completed, the reactor was pressurized with hydrogen to 100 psig and mixture was heated to 50° C. (jacket temperature) and stirred at a speed to ensure good mixing. The reaction mixture was aged at 100 psig H$_2$ and 50° C. for 23 h (reactor pressure jumped to ~200 psig due to soluble ammonia in the mixture). The mixture was then cooled to 20° C. then filtered then transferred to a 100 ml 3-necked flask. To the mixture water (0.55 mL) was added drop wise, which resulted in yellow slurry. The resulting slurry was stirred for 30 min then filtered, then the titanium dioxide cake was washed with 1,4-dioxane (30 mL). The filtrate was collected and the solvent was removed. The resulting oil was dissolved in isopropanol (40 mL). To the solution ~5N HCl in isopropanol (9.0 ml) was added drop wise resulting in a thick slurry. To the slurry isopropyl acetate (60 ml) was added and heated to 45° C. for 10 min and then cooled to 22° C. over approximately 3 h to afford a white solid (3.0 g, 51.5%). $^1$H NMR (500 MHz, CD$_3$OD) δ ppm 8.89 (d, J=5.3, 1H), 8.42 (bs, 1H), 8.05 (bs, 1H), 7.35 (dd, J=8.19, 16.71), 7.2 (bs, 2H), 7.22 (m, 1H) 7.15 (m, 1H), 5.7 (dd, J=1.89, J=8.51), 5.4 (m, 1H), 3.5 (m, 1H), 1.9-2.5 (B, 4 h) 1.4 (sept, J=15.13, 3H), 1.2 (t, J=7.57 18H); $^{13}$C NMR (125 MHz, CD$_3$OD) δ 153.5, 151.6, 151.5, 151.3, 149.4, 143.4, 135.03, 129.8, 129.8, 127.8, 126.8, 126.4, 118.6, 72.4, 54.1, 41.4, 34.3, 32.3, 25.4, 18.6, 18.5, 13.7, 13.6, 13.5, 13.3.

Example 2

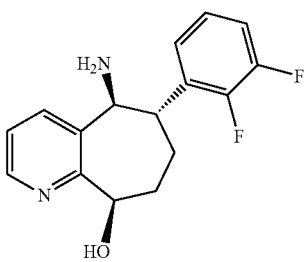 [SMILES: N[C@@H]1c2cccnc2[C@H](O)CC[C@H]1c1cccc(F)c1F]

(6S,9R)-5-amino-6-(2,3-difluorophenyl)-6,7,8,9-tetrahydro-5H-cyclohepta[b]pyridin-9-ol To a 250 ml flask was charged (6S,9R)-6-(2,3-difluorophenyl)-9-(triisopropylsilyloxy)-6,7,8,9-tetrahydro-5H-cyclohepta[b]pyridin-5-amine di HCl salt (15 g, 25.88 mmol) and a solution of isopropanol:water (45 mL:15 mL). The mixture was heated to 82° C. for 6 h then dried via azeotropic distillation at atmospheric pressure using isopropanol until the KF was less than <3%. After fresh isopropanol (25 ml) was added, the mixture was heated to 70° C. and then isopropyl acetate (45 ml) was added that resulting in a white slurry. The slurry cooled to 22° C. for 15 min to afford a white solid (9.33 g, 99%). $^1$H NMR (500 MHz CD$_3$OD) δ 8.77 (d, J=5.7 Hz, 1H), 8.47 (d, J=7.9 Hz, 1H), 8.11 (dd, J=6.0, 8.2 Hz, 1H), 7.21-7.32 (m, 3H), 5.53 (dd, J=3.8, 9.8 Hz, 1H) 5.33 (d, J=9.8 Hz, 1H), 3.5 (bm, 1H), 2.25-2.40 (m, 2H), 2.15 (bm, 1H), 1.90 (bm, 1H); $^{13}$C NMR (125 MHz, MeOD) δ 159.4, 153.9, 151.9 and 151.8, 149.7, 143.6, 141.8, 135.7, 130.6, 127.7, 126.8, 118.9, 70.0, 54.9, 42.2, 34.5, 33.4.

Example 3

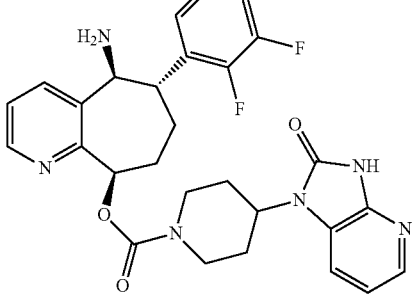

(5S,6S,9R)-5-amino-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate To a round bottom flask was charged (5S,6S,9R)-5-amino-6-(2,3-difluorophenyl)-6,7,8,9-tetrahydro-5H-cyclohepta[b]pyridin-9-ol dihydrochloride (1.00 g, 2.73 mmol) and dichloromethane (15 mL). A solution of sodium carbonate (0.58 g, 5.47 mmol), 20 wt % aqueous sodium chloride (5 mL), and water (10 mL) was added and the biphasic mixture was aged for 30 min. The phases were allowed to separate and the organic stream was retained. The dichloromethane solvent was then switched with azeotropic drying to tetrahydrofuran, with a final volume of (15 mL). At 20° C. was added, 1-(1-(1H-imidazole-1-carbonyl)piperidin-4-yl)-1H-imidazo[4,5-b]pyridin-2(3H)-one (0.95 g, 3.01 mmol), followed by a 20 wt % potassium tert-butoxide solution in THF (4 mL, 6.20 mmol). The thin slurry was aged for 1 h, and then the reaction was quenched with the addition of 20 wt % aqueous sodium chloride (5 mL) and 20 wt % aqueous citric acid (2.5 mL). The layers were allowed to separate and the organic rich layer was retained. The organic layer was washed with 20 wt % aqueous sodium chloride (15 mL). The organic tetrahydrofuran stream was then concentrated in vacuo to afford an oil which was resuspended in dichloromethane (20 mL) and dried with MgSO$_4$. The dichloromethane stream was concentrated in vacuo to afford an oil, which was crystallized from ethanol: heptane to afford a white solid (1.14 g, 78.3%). LCMS: [M+H]=535: $^1$H NMR (600 MHz, d$_6$-DMSO) δ 11.58 (1H, bs), 8.45 (1H, bd), 8.03 (1H, d, J=7.3 Hz), 7.91 (1H, bs), 7.54 (1H, bd), 7.36 (1H, bm), 7.34 (1H, bm), 7.28 (1H, m), 7.21 (1H, m), 7.01 (1H, bs), 6.01 (1H, dd, J=3.2, 9.8 Hz), 4.48 (1H, d, J=9.5 Hz), 4.43 (1H, bm), 4.38 (1H, bm), 4.11 (1H, bm), 3.08 (1H, bm), 2.93 (1H, bm), 2.84 (1H, m), 2.62 (1H, bm), 2.20 (2H, bm), 2.13 (1H, bm), 2.12 (1H, bm), 1.75 (1H, bm), 1.72 (1H, bm), 1.66 (1H, bm); $^{13}$C NMR (125 MHz, d$_6$-DMSO) δ 156.6, 154.2, 153.0, 149.8, 148.1, 146.4, 143.5, 139.6, 137.4, 134.0, 132.8, 124.7, 124.5, 123.3, 122.2, 116.3, 115.0, 114.3, 73.7, 52.8, 50.0, 43.8, 43.3, 32.0, 30.3, 28.6; mp 255° C.

Example 4

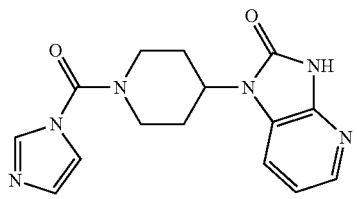 [SMILES: O=C(N1CCC(n2c(=O)[nH]c3ncccc32)CC1)n1ccnc1]

1-(1-(1H-imidazole-1-carbonyl)piperidin-4-yl)-1H-imidazo[4,5-b]pyridin-2(3H)-one To a round bottom flask was added, 1,1'-carbonyldiimidazole (8.59 g, 51.4 mmol), diisopropylethylamine (12.6 mL, 72.2 mmol) and tetrahydrofuran (100 mL). This mixture was warmed to 40° C. and aged for 10 min, after which 1-(piperidin-4-yl)-1H-imidazo[4,5-b]pyridin-2(3H)-one dihydrochloride (10 g, 34.3 mmol) was added. The slurry was aged at 40° C. for 3 h, and then upon reaction completion, the solvent was swapped to acetonitrile which afforded an off white solid (9.19 g, 85.9%). LCMS: [M+H]=313; $^1$H NMR (400 MHz, d$_6$-DMSO) δ 11.58 (1H, s), 8.09 (1H, s), 7.97 (1H, d, J=8.0 Hz), 7.73 (1H, d, J=4.0 Hz), 7.53 (1H, s), 7.05 (1H, s), 7.00 (1H, dd, J=4.0, 8.0 Hz), 4.52, (1H, dd, J=8.0, 12.0 Hz), 4.05 (2H, bd, J=8.0 Hz), 3.31 (2H, m), 2.34 (2H, m), 1.82 (2H, bd, J=12.0 Hz); $^{13}$C NMR (100 MHz, d$_6$-DMSO) δ 153.0, 150.4, 143.4, 139.8, 137.2, 128.9, 123.0, 118.7, 116.4, 115.2, 49.3, 45.1, 28.5; mp 226° C.

Example 5

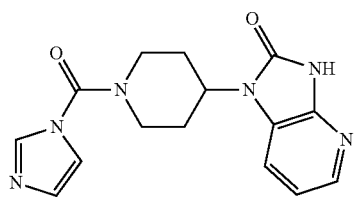 [SMILES: O=C(N1CCC(n2c(=O)[nH]c3ncccc32)CC1)n1ccnc1]

1-(1-(1H-imidazole-1-carbonyl)piperidin-4-yl)-1H-imidazo[4,5-b]pyridin-2(3H)-one To a 250 ml round bottom flask was added 3-N-piperidin-4-ylpyridine-2,3-diamine dihydrochloride (10 g, 52 mmol) and acetonitrile (100 mL). Triethyl amine (11.44 g, 113 mmol) and 1,1'-Carbonyldiimidazole (18.34 g, 113 mmol) were added at ambient temperature and the mixture was stirred for 2 h. The solvent was evaporated under vacuum to ~30 ml reaction volume and isopropyl acetate (50 mL) was added into the resulting slurry at 40° C. The slurry was cooled to 10-15° C. and then stirred for 1 h to afford an off white solid (10 g, 85%).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula II, or a salt thereof, where Ar$^1$ is phenyl substituted with 0-3 substituents selected from the group consisting of cyano, halo, alkyl, haloalkyl, alkoxy, haloalkoxy, and alkylSO$_2$ and R$^1$ is hydrogen or trialkylsilyl, alkoxy, alkylcarbonyl, benzyl, benzoyl, and pivaloyl

2. The compound of claim 1 where Ar$^1$ is 2,3-difluorophenyl.
3. The compound of claim 2 which is the dihydrochloride salt.
4. The compound of claim 1 where R$^1$ is triisopropylsilyl.
5. The compound of claim 4 which is the dihydrochloride salt.
6. The compound of claim 1 where R$^1$ is hydrogen.
7. The compound of claim 6 which is the dihydrochloride salt.
8. A compound of formula II, or a salt thereof, having the following formula:

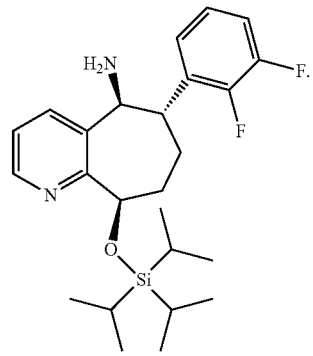 [SMILES: CC(C)[Si](O[C@@H]1CC[C@@H](c2cccc(F)c2F)[C@H](N)c2cccnc21)(C(C)C)C(C)C]

9. The compound of claim 8 which is the dihydrochloride salt.

* * * * *